(12) United States Patent
Molaei et al.

(10) Patent No.: US 8,864,815 B2
(45) Date of Patent: *Oct. 21, 2014

(54) MEDICAL DEVICES INCLUDING METALLIC FILM AND AT LEAST ONE FILAMENT

(75) Inventors: Masoud Molaei, Mountain View, CA (US); Beren W. Correa, Fremont, CA (US)

(73) Assignee: Boston Scientific Scimed, Inc., Maple Grove, CA (US)

( * ) Notice: Subject to any disclaimer, the term of this patent is extended or adjusted under 35 U.S.C. 154(b) by 887 days.

This patent is subject to a terminal disclaimer.

(21) Appl. No.: 13/031,923

(22) Filed: Feb. 22, 2011

(65) Prior Publication Data

US 2011/0144740 A1    Jun. 16, 2011

Related U.S. Application Data

(63) Continuation of application No. 11/025,684, filed on Dec. 29, 2004, now Pat. No. 7,901,447.

(51) Int. Cl.
*A61F 2/82* (2013.01)
*A61F 2/90* (2013.01)
*A61F 2/07* (2013.01)

(52) U.S. Cl.
CPC .............. *A61F 2/07* (2013.01); *A61F 2002/072* (2013.01); *A61F 2002/075* (2013.01); *A61F 2/90* (2013.01); *Y10S 623/901* (2013.01)
USPC .......................................... 623/1.15; 623/901

(58) Field of Classification Search
CPC ...................................... A61F 2/06; A61F 2/82
USPC ................... 623/1.11–135; 424/423
See application file for complete search history.

(56) References Cited

U.S. PATENT DOCUMENTS

| 4,793,348 | A | 12/1988 | Palmaz |
| 4,864,824 | A | 9/1989 | Gabriel et al. |
| 5,035,706 | A | 7/1991 | Giantureo et al. |
| 5,061,914 | A | 10/1991 | Busch et al. |
| 5,085,535 | A | 2/1992 | Solberg et al. |
| 5,119,555 | A | 6/1992 | Johnson |
| 5,245,738 | A | 9/1993 | Johnson |
| 5,302,261 | A | 4/1994 | LeRoy et al. |
| 5,306,294 | A | 4/1994 | Winston et al. |
| 5,325,880 | A | 7/1994 | Johnson et al. |

(Continued)

FOREIGN PATENT DOCUMENTS

| EP | 0 472 731 | 8/1991 |
| EP | 0 792 627 A2 | 9/1997 |

(Continued)

OTHER PUBLICATIONS

0566WO1 ISR—PCT/US2005/007282 mailed Jul. 5, 2005, 15 pages.

(Continued)

*Primary Examiner* — Suzette J Gherbi
(74) *Attorney, Agent, or Firm* — Kacvinsky Daisak Bluni PLLC

(57) ABSTRACT

Medical devices, such as endoprostheses, and methods of making the devices are disclosed. The medical device can include a composite cover formed of a deposited metallic film. The cover may include one or more filaments, e.g., wires, which cooperate with the film to provide desirable mechanical properties. The wires may be integrated with the film by depositing the film over the wires.

21 Claims, 10 Drawing Sheets

(56) References Cited

U.S. PATENT DOCUMENTS

| | | |
|---|---|---|
| 5,382,261 A | 1/1995 | Palmaz |
| 5,405,378 A | 4/1995 | Strecker et al. |
| 5,441,515 A | 8/1995 | Khosravi et al. |
| 5,518,680 A | 5/1996 | Cima et al. |
| 5,554,182 A | 9/1996 | Dinh et al. |
| 5,556,413 A | 9/1996 | Lam |
| 5,607,466 A | 3/1997 | Imbert et al. |
| 5,619,177 A | 4/1997 | Johnson et al. |
| 5,656,036 A | 8/1997 | Palmaz |
| 5,667,523 A | 9/1997 | Bynon et al. |
| 5,674,242 A | 10/1997 | Phan et al. |
| 5,676,697 A | 10/1997 | McDonald |
| 5,728,150 A | 3/1998 | McDonald et al. |
| 5,755,734 A | 5/1998 | Richter et al. |
| 5,800,517 A | 9/1998 | Anderson et al. |
| 5,817,102 A | 10/1998 | Johnson et al. |
| 5,824,042 A | 10/1998 | Lombardi et al. |
| 5,824,049 A | 10/1998 | Ragheb et al. |
| 5,824,054 A | 10/1998 | Khosravi et al. |
| RE35,988 E | 12/1998 | Winston et al. |
| 5,843,158 A | 12/1998 | Lenker et al. |
| 5,843,164 A | 12/1998 | Frantzen et al. |
| 5,843,289 A | 12/1998 | Lee et al. |
| 5,849,206 A | 12/1998 | Amon et al. |
| 5,860,998 A | 1/1999 | Robinson et al. |
| 5,865,723 A | 2/1999 | Love |
| 5,882,444 A | 3/1999 | Flomenblit et al. |
| 5,888,734 A | 3/1999 | Cremer et al. |
| 5,897,911 A | 4/1999 | Loeffler |
| 5,903,099 A | 5/1999 | Johnson et al. |
| 5,938,697 A | 8/1999 | Killion et al. |
| 5,941,249 A | 8/1999 | Maynard |
| 5,957,929 A | 9/1999 | Brenneman |
| 5,984,963 A | 11/1999 | Ryan et al. |
| 6,007,573 A | 12/1999 | Wallace et al. |
| 6,015,431 A | 1/2000 | Thornton et al. |
| 6,015,433 A | 1/2000 | Roth |
| 6,017,977 A | 1/2000 | Evans et al. |
| 6,036,725 A | 3/2000 | Avellanet |
| 6,043,451 A | 3/2000 | Julien et al. |
| 6,048,622 A | 4/2000 | Hagood et al. |
| 6,059,766 A | 5/2000 | Greff |
| 6,077,298 A | 6/2000 | Tu et al. |
| 6,096,175 A | 8/2000 | Roth |
| 6,099,561 A | 8/2000 | Alt |
| 6,107,004 A | 8/2000 | Donadio, III |
| 6,120,535 A | 9/2000 | McDonald et al. |
| 6,132,460 A | 10/2000 | Thompson |
| 6,133,547 A | 10/2000 | Maynard |
| 6,139,564 A | 10/2000 | Teoh |
| 6,143,022 A | 11/2000 | Shull et al. |
| 6,159,239 A | 12/2000 | Greenhalgh |
| 6,174,330 B1 | 1/2001 | Stinson |
| 6,190,404 B1 | 2/2001 | Palmaz et al. |
| 6,206,911 B1 | 3/2001 | Milo |
| 6,224,627 B1 | 5/2001 | Armstrong et al. |
| 6,224,630 B1 | 5/2001 | Bao et al. |
| 6,245,104 B1 | 6/2001 | Alt |
| 6,254,628 B1 | 7/2001 | Wallace et al. |
| 6,258,117 B1 | 7/2001 | Camrud et al. |
| 6,290,720 B1 | 9/2001 | Khosravi et al. |
| 6,303,100 B1 | 10/2001 | Ricci et al. |
| 6,315,788 B1 | 11/2001 | Roby |
| 6,315,794 B1 | 11/2001 | Richter |
| 6,355,055 B1 | 3/2002 | Waksman et al. |
| 6,379,383 B1 | 4/2002 | Palmaz et al. |
| 6,398,803 B1 | 6/2002 | Layne et al. |
| 6,406,487 B2 | 6/2002 | Brenneman |
| 6,406,490 B1 | 6/2002 | Roth |
| 6,409,749 B1 | 6/2002 | Maynard |
| 6,428,569 B1 | 8/2002 | Brown |
| 6,447,478 B1 | 9/2002 | Maynard |
| 6,454,738 B1 | 9/2002 | Tran et al. |
| 6,458,152 B1 | 10/2002 | Khosravi et al. |
| 6,458,153 B1 | 10/2002 | Bailey et al. |
| 6,471,980 B2 | 10/2002 | Sirhan et al. |
| 6,485,510 B1 | 11/2002 | Camrud et al. |
| 6,506,211 B1 | 1/2003 | Skubitz et al. |
| 6,520,984 B1 | 2/2003 | Garrison et al. |
| 6,527,919 B1 | 3/2003 | Roth |
| 6,533,905 B2 | 3/2003 | Johnson et al. |
| 6,537,310 B1 | 3/2003 | Palmaz et al. |
| 6,605,111 B2 | 8/2003 | Bose et al. |
| 6,614,570 B2 | 9/2003 | Johnson et al. |
| 6,618,921 B1 | 9/2003 | Thornton |
| 6,620,192 B1 | 9/2003 | Jalisi |
| 6,620,634 B2 | 9/2003 | Johnson et al. |
| 6,624,730 B2 | 9/2003 | Johnson et al. |
| 6,629,993 B2 | 10/2003 | Voinov |
| 6,632,240 B2 | 10/2003 | Khosravi et al. |
| 6,638,301 B1 | 10/2003 | Chandrasekaran et al. |
| 6,666,882 B1 | 12/2003 | Bose et al. |
| 6,669,719 B2 | 12/2003 | Wallace et al. |
| 6,669,721 B1 | 12/2003 | Bose et al. |
| 6,669,795 B2 | 12/2003 | Johnson et al. |
| 6,673,102 B1 * | 1/2004 | Vonesh et al. ............ 623/1.13 |
| 6,676,987 B2 | 1/2004 | Zhong et al. |
| 6,695,865 B2 | 2/2004 | Boyle et al. |
| 6,699,278 B2 | 3/2004 | Fischell et al. |
| 6,699,279 B2 | 3/2004 | Stevens et al. |
| 6,746,478 B2 | 6/2004 | Jayaraman |
| 6,752,826 B2 | 6/2004 | Holloway et al. |
| 6,767,418 B1 | 7/2004 | Zhang et al. |
| 6,776,795 B2 | 8/2004 | Pelton |
| 6,820,676 B2 | 11/2004 | Palmaz et al. |
| 6,849,085 B2 | 2/2005 | Marton |
| 6,936,066 B2 | 8/2005 | Palmaz et al. |
| 6,953,560 B1 | 10/2005 | Castro et al. |
| 7,105,018 B1 | 9/2006 | Yip et al. |
| 7,279,175 B2 | 10/2007 | Chen et al. |
| 7,410,497 B2 | 8/2008 | Hastings et al. |
| 7,632,303 B1 * | 12/2009 | Stalker et al. ............ 623/1.19 |
| 7,901,447 B2 * | 3/2011 | Molaei et al. ............ 623/1.15 |
| 7,947,071 B2 | 5/2011 | Schmid et al. |
| 2001/0001834 A1 | 5/2001 | Palmaz et al. |
| 2001/0032013 A1 | 10/2001 | Marton |
| 2001/0039449 A1 | 11/2001 | Johnson et al. |
| 2001/0044647 A1 | 11/2001 | Pinchuk et al. |
| 2002/0007958 A1 | 1/2002 | Rivelli et al. |
| 2002/0017503 A1 | 2/2002 | Banas et al. |
| 2002/0019662 A1 | 2/2002 | Brauckman et al. |
| 2002/0035774 A1 | 3/2002 | Austin |
| 2002/0042645 A1 | 4/2002 | Shannon |
| 2002/0046783 A1 | 4/2002 | Johnson et al. |
| 2002/0142119 A1 | 10/2002 | Seward et al. |
| 2002/0151965 A1 | 10/2002 | Roth |
| 2002/0161342 A1 | 10/2002 | Rivelli, Jr. et al. |
| 2002/0162605 A1 | 11/2002 | Horton et al. |
| 2002/0165576 A1 | 11/2002 | Boyle et al. |
| 2002/0165600 A1 | 11/2002 | Banas et al. |
| 2002/0173809 A1 | 11/2002 | Fleischman et al. |
| 2002/0187288 A1 | 12/2002 | Lim et al. |
| 2002/0193869 A1 | 12/2002 | Dang |
| 2002/0195579 A1 | 12/2002 | Johnson |
| 2002/0198584 A1 | 12/2002 | Unsworth et al. |
| 2003/0002994 A1 | 1/2003 | Johnson et al. |
| 2003/0004567 A1 | 1/2003 | Boyle et al. |
| 2003/0018354 A1 | 1/2003 | Roth et al. |
| 2003/0023303 A1 | 1/2003 | Palmaz et al. |
| 2003/0040791 A1 | 2/2003 | Oktay |
| 2003/0050691 A1 | 3/2003 | Shifrin et al. |
| 2003/0059640 A1 | 3/2003 | Marton et al. |
| 2003/0060782 A1 | 3/2003 | Bose et al. |
| 2003/0074049 A1 | 4/2003 | Hoganson et al. |
| 2003/0078649 A1 | 4/2003 | Camrud et al. |
| 2003/0083731 A1 | 5/2003 | Kramer et al. |
| 2003/0127318 A1 | 7/2003 | Johnson et al. |
| 2003/0130718 A1 | 7/2003 | Palmas et al. |
| 2003/0130721 A1 | 7/2003 | Martin et al. |
| 2003/0139797 A1 | 7/2003 | Johnson et al. |
| 2003/0153971 A1 | 8/2003 | Chandrasekaran |
| 2003/0159920 A1 | 8/2003 | Roth |
| 2003/0185895 A1 | 10/2003 | Lanphere et al. |
| 2003/0187495 A1 | 10/2003 | Cully et al. |

(56) References Cited

U.S. PATENT DOCUMENTS

| | | |
|---|---|---|
| 2003/0212430 A1 | 11/2003 | Bose et al. |
| 2004/0006381 A1 | 1/2004 | Sequin et al. |
| 2004/0014253 A1 | 1/2004 | Gupta et al. |
| 2004/0030377 A1 | 2/2004 | Dubson et al. |
| 2004/0034408 A1 | 2/2004 | Majercak et al. |
| 2004/0054399 A1 | 3/2004 | Roth et al. |
| 2004/0054406 A1 | 3/2004 | Dubson et al. |
| 2004/0059410 A1 | 3/2004 | Cox |
| 2004/0098095 A1 | 5/2004 | Burnside et al. |
| 2004/0107004 A1 | 6/2004 | Levine et al. |
| 2004/0143317 A1 | 7/2004 | Stinson et al. |
| 2004/0199239 A1 | 10/2004 | Austin et al. |
| 2004/0225350 A1 | 11/2004 | Shanley |
| 2004/0254520 A1 | 12/2004 | Porteous et al. |
| 2005/0004653 A1 | 1/2005 | Gerberding et al. |
| 2005/0010275 A1 | 1/2005 | Sahatjian et al. |
| 2005/0033399 A1 | 2/2005 | Richter |
| 2005/0165468 A1 | 7/2005 | Marton |
| 2005/0165469 A1 | 7/2005 | Hogendijk |
| 2005/0197687 A1 | 9/2005 | Molaei et al. |
| 2005/0197689 A1 | 9/2005 | Molaei et al. |
| 2005/0197690 A1 | 9/2005 | Molaei et al. |
| 2006/0069428 A1 | 3/2006 | Feller |
| 2006/0100659 A1 | 5/2006 | Dinh et al. |
| 2006/0115514 A1 | 6/2006 | Gengrinovitch |
| 2006/0122691 A1 | 6/2006 | Richter |
| 2006/0142838 A1 | 6/2006 | Molaei et al. |
| 2006/0142842 A1* | 6/2006 | Molaei et al. ............... 623/1.15 |
| 2006/0142845 A1 | 6/2006 | Molaei et al. |
| 2006/0142851 A1 | 6/2006 | Molaei et al. |
| 2006/0147492 A1 | 7/2006 | Hunter et al. |
| 2006/0184231 A1 | 8/2006 | Rucker |
| 2006/0259131 A1 | 11/2006 | Molaei et al. |
| 2006/0271158 A1 | 11/2006 | Olson |
| 2007/0016283 A1 | 1/2007 | Greenhalgh et al. |
| 2007/0073385 A1 | 3/2007 | Schaeffer et al. |
| 2007/0112411 A1 | 5/2007 | Obermiller et al. |
| 2007/0250156 A1 | 10/2007 | Palmaz |
| 2008/0027388 A1 | 1/2008 | Banas et al. |
| 2008/0221665 A1 | 9/2008 | Peckham et al. |
| 2009/0132022 A1 | 5/2009 | Banas |
| 2009/0187240 A1 | 7/2009 | Clerc et al. |
| 2010/0030320 A1* | 2/2010 | Feller, III ............... 623/1.11 |
| 2011/0054590 A1 | 3/2011 | Leopold et al. |

FOREIGN PATENT DOCUMENTS

| | | |
|---|---|---|
| EP | 1 604 697 | 12/2005 |
| EP | 1 725 186 | 11/2006 |
| EP | 1 725 187 | 11/2006 |
| EP | 1 725 188 | 11/2006 |
| GB | 2 125 442 A | 3/1984 |
| JP | 2003/102849 | 8/2003 |
| JP | 2007/502069 | 9/2007 |
| JP | 2007/526098 | 9/2007 |
| JP | 2007/526099 | 9/2007 |
| WO | WO 96/06814 | 3/1996 |
| WO | WO 98/53362 | 11/1998 |
| WO | WO 99/02092 | 1/1999 |
| WO | WO 99/60267 | 12/1999 |
| WO | WO 99/62432 | 12/1999 |
| WO | WO 00/62711 | 10/2000 |
| WO | WO 01/21097 | 3/2001 |
| WO | WO 01/53559 | 7/2001 |
| WO | WO 01/87371 | 11/2001 |
| WO | WO 01/89420 | 11/2001 |
| WO | WO 01/91823 | 12/2001 |
| WO | WO 01/95697 | 12/2001 |
| WO | WO 02/34163 | 5/2002 |
| WO | WO 02/38080 | 5/2002 |
| WO | WO 02/38086 | 5/2002 |
| WO | WO 02/060506 | 8/2002 |
| WO | WO 03/003943 | 1/2003 |
| WO | WO 03/011363 | 2/2003 |
| WO | WO 03/013337 | 2/2003 |
| WO | WO 03/015840 | 2/2003 |
| WO | WO 03/018100 | 3/2003 |
| WO | WO 03/075793 | 9/2003 |
| WO | WO 03/075799 A1 | 9/2003 |
| WO | WO 03/099161 A2 | 12/2003 |
| WO | WO 2004/002370 A1 | 1/2004 |
| WO | WO 2004/008504 | 1/2004 |
| WO | WO 2004/028340 | 4/2004 |
| WO | 2005/084583 | 9/2005 |
| WO | 2005/084584 | 9/2005 |
| WO | 2005/084585 | 9/2005 |
| WO | 2006/125022 | 4/2006 |
| WO | 2006/071215 | 7/2006 |
| WO | 2006/071242 | 7/2006 |
| WO | 2006/071243 | 7/2006 |
| WO | 2006/071244 | 7/2006 |
| WO | 2006/071245 | 7/2006 |

OTHER PUBLICATIONS

0567WO1 ISR—PCT/US2005/006993 mailed Aug. 2, 2005, 21 pages.

0568WO1 ISR—PCT/US2005/007161 mailed Jul. 28, 2005, 45 pages.

0569WO1 ISR—PCT/US2005/007173 mailed Dec. 6, 2005, 19 pages.

0570WO1 ISR—PCT/US2005/007164 mailed Jul. 5, 2005, 13 pages.

0596WO1 ISR—PCT/US2005/007162 mailed Oct. 4, 2005, 16 pages.

0621WO1 ISR—PCT/US2005/006895 mailed Mar. 2, 2005, 16 pages.

0627WO1 ISR—PCT/US2006/019126 mailed Feb. 1, 2007, 16 pages.

Dieter, George, *Mechanical Metallurgy*, Singapore, McGraw-Hill Book Co., 10$^{th}$ Printing 1984, pp. 111-117, 142-145, and 234-237. TA405.D53.

Freiherr, Greg, "Shape-Memory Alloys Offer Untapped", Medical Device & Diagnostic Industry Magazine, Mar. 1998, 5 pages [retrieved on Jun. 30, 2004].

Fu et al., "TiNi-based thin films in MEMS applications: a review", Sensors and Actuators, Article in Press, Elsevier, Feb. 2004, 14 pages.

Gertner et al., "Drug Delivery from Electrochemically Deposited Thin Metal Films", Electrochemical and Sold-State Letter, 6 (4) J4-J6, 2003.

Gertner et al., "Electrochemistry and Medical Devices: Friend or Foe?", The Electrochemical Society Interface, Fall 2003, pp. 20-24.

Gupta et al., "Nitinol Thin Film Three-Dimensional Devices—Fabrication and Applications", http://www.tinialloy.com/pdf/smst.pdf, Sep. 7, 2003 [retrieved Dec. 1, 2004].

He et al., "$CO_2$ laser annealing of sputtering deposited NiTi shape memory thin films", Journal of Micromechanics and Microengineering, May 20, 2004, pp. 950-956.

Kaczmarek, S. M., "Pulsed laser deposition—today and tomorrow", STL'96, Proc. SPIE, vol. 3187, 1997, pp. 129-134.

Krebs et al., "Pulsed Laser Deposition (PLD)—a Versatile Thin Film Technique", Advances in Solid State Physics 2003, 43, 505-517.

Nakayama et al., "Fabrication of micropored elastomeric film-covered stents and acute-phase performances", Journal of Biomedical Mateirals Research Part A, vol. 64A, Issue 1, Sep. 30, 2002, pp. 52-61.

Neocera, Inc. Brochure—Pulsed Laser Deposition, www.neocera.com [retrieved Dec. 1, 2004].

Padhi et al., "Planarization of Copper Thin Films by Electropolishing in Phosphoric Acid for ULSI Application", Journal of Electrochemical Society, vol. 150, 2003, pp. G10-G14.

Pelleiter et al., "Effect of high energy argon implantation into NiTi shape memory alloy", Surface and Coatings Technology, 158-159, 2002, pp. 301-308.

(56) References Cited

OTHER PUBLICATIONS

Ren et al., "Carbon nitride materials synthesized by Ion-assisted pulsed laser deposition", Riken Review No. 43, Jan. 2002, pp. 41-44.
Schetky et al., "Issues in the Further Development of Nitinol Properties and Processing for Medical Device Application", Proceedings, ASM Materials & Processes for Medical Devices Conference, Anaheim, in press, 2003, 6 pages.
Shabalovskaya et al., "Comparative performances of Nitinol surfaces in protein adsorption and platelet adhesion—Preliminary results", Institute for Physical Research and Technology, Ames Laboratory, Ames, IA University of Washington, Seattle WA Memry Corporation, Bethel CT, 2004, 10 pages.
Stoeckel et al., "A survey of stent designs", Min Invas Ther & Allied Technol, 11(4), 2002, pp. 137-147.

* cited by examiner

MEDICAL DEVICES INCLUDING METALLIC FILM AND AT LEAST ONE FILAMENT

CROSS REFERENCE TO RELATED APPLICATION

This application is a continuation of U.S. patent application Ser. No. 11/025,684, filed Dec. 29, 2004. The disclosure of the prior application is hereby incorporated by reference in its entirety.

FIELD OF THE INVENTION

The invention relates to medical devices, such as endoprostheses, and methods of making the devices.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a radially compacted condition. Upon reaching the desired implantation site, the restraint is removed, for example, by retracting a restraining device such as an outer sheath, enabling the endoprosthesis to self-expand by its own internal elastic restoring force.

SUMMARY OF THE INVENTION

The invention relates to medical devices, such as endoprostheses, and methods of making the devices. Exemplary endoprostheses include stents, covered stents, and stent-grafts.

In some embodiments, an endoprosthesis includes a deposited metallic film defining first and second opposed surfaces and a thickness of less than about 50 µm therebetween and at least one metal filament. The at least one filament defines a length. At least a portion of the filament along its length is embedded within the deposited metallic film between its first and second surfaces.

The deposited metallic film may include deposited titanium and nickel, e.g., an alloy including nickel and titanium.

The deposited film may have a substantially tubular shape defining a longitudinal axis. The at least one filament may extend, e.g., linearly or helically, generally along the longitudinal axis.

The tubular shape of the film may define a length along the longitudinal axis and the length of the filament may be at least about 30% of the length of the tubular shape of the film.

The endoprosthesis may include a plurality of filaments each defining a length. At least a portion of each wire along its length may be embedded within the metallic film between the first and second surfaces. Each filament may extend generally along the longitudinal axis. The length of each filament may be at least 30% of the length of the tubular shape of the film.

At least 75% of the filament along its length may be embedded within the metallic film between the first and second surfaces of the metallic film.

The filament, along its length, may include a plurality of embedded portions and at least one non-embedded portion. Each embedded portion may be embedded within the metallic film between the first and second surfaces of the metallic film. Adjacent embedded portions may be spaced apart by a non-embedded portion of the filament.

The substantially tubular shape may define a circumference. The at least one filament may extend at least partially about the circumference.

The at least one filament may be an alloy comprising nickel and titanium.

The metallic film and the at least one filament may each have a respective tensile strength, with the tensile strength of the filament being greater than the tensile strength of the metallic film. The metallic film and the at least one filament may each have a respective, different shape set configuration.

The endoprosthesis may include a stent body. The stent body and the deposited film may be generally concentric.

In some embodiments, an endoprosthesis includes a cover including at least one deposited metallic film. The cover defines first and second opposed metallic film edges. The first and second opposed metallic film edges each define a channel. At least one filament may extend along the channel of each opposed metallic film edge.

The deposited metallic film may include deposited nickel and titanium, e.g., an alloy including nickel and titanium.

The cover may have a substantially tubular shape defining a longitudinal axis. The at least one filament may extend generally parallel to the longitudinal axis. The tubular shape may define a length along the longitudinal axis. The length of the filament may be at least about 30% of the length of the tubular shape.

The first and second opposed edges may each define at least one offset tab. The channel of each opposed edge may be formed by the offset tab.

The first and second opposed edges may each define a plurality of channels. Each channel may be formed by a respective offset tab. The filament may extend through at least some of the channels of each opposed edge.

The endoprosthesis may include a stent body. At least a portion of the at least one filament and at least a portion of the stent body may be secured together.

The filament may define a longitudinal axis. An engagement between at least one of the channels and the filament may restrict movement of the filament along its longitudinal axis with respect to the at least one of the channels. The filament may have freedom of movement along its length with respect to at least one of the channels.

The first and second opposed edges may be a first pair of opposed edges and metallic film of the cover may define a plurality of pairs of first and second opposed edges. Each edge of each pair may define at least one channel. A respective filament may extend through the channel of each opposed edge of each pair. Each pair of opposed edges may extend generally along the longitudinal axis. Each filament may have a length at least about 30% of the length of the tubular shape. The first and second edges of each pair of opposed edges may have at least some relative freedom of movement with respect to a circumference of the cover.

In one aspect, the invention features an endoprosthesis including a metallic film, e.g., a vapor deposited film, including nickel, titanium, and chromium. A ratio of a weight of chromium of the metallic film to a combined weight of nickel, titanium, and chromium of the metallic film is at least 0.001 and can be less than 0.0075.

Other aspects, features, and advantages of the invention will be apparent from the description of the preferred embodiments thereof and from the claims.

BRIEF DESCRIPTION OF THE FIGURES

FIG. 3b is a cross-sectional view of the endoprosthesis of FIG. 3a.

FIG. 10b is a cross-sectional view of the endoprosthesis of FIG. 10a.

DETAILED DESCRIPTION

Figure 1:
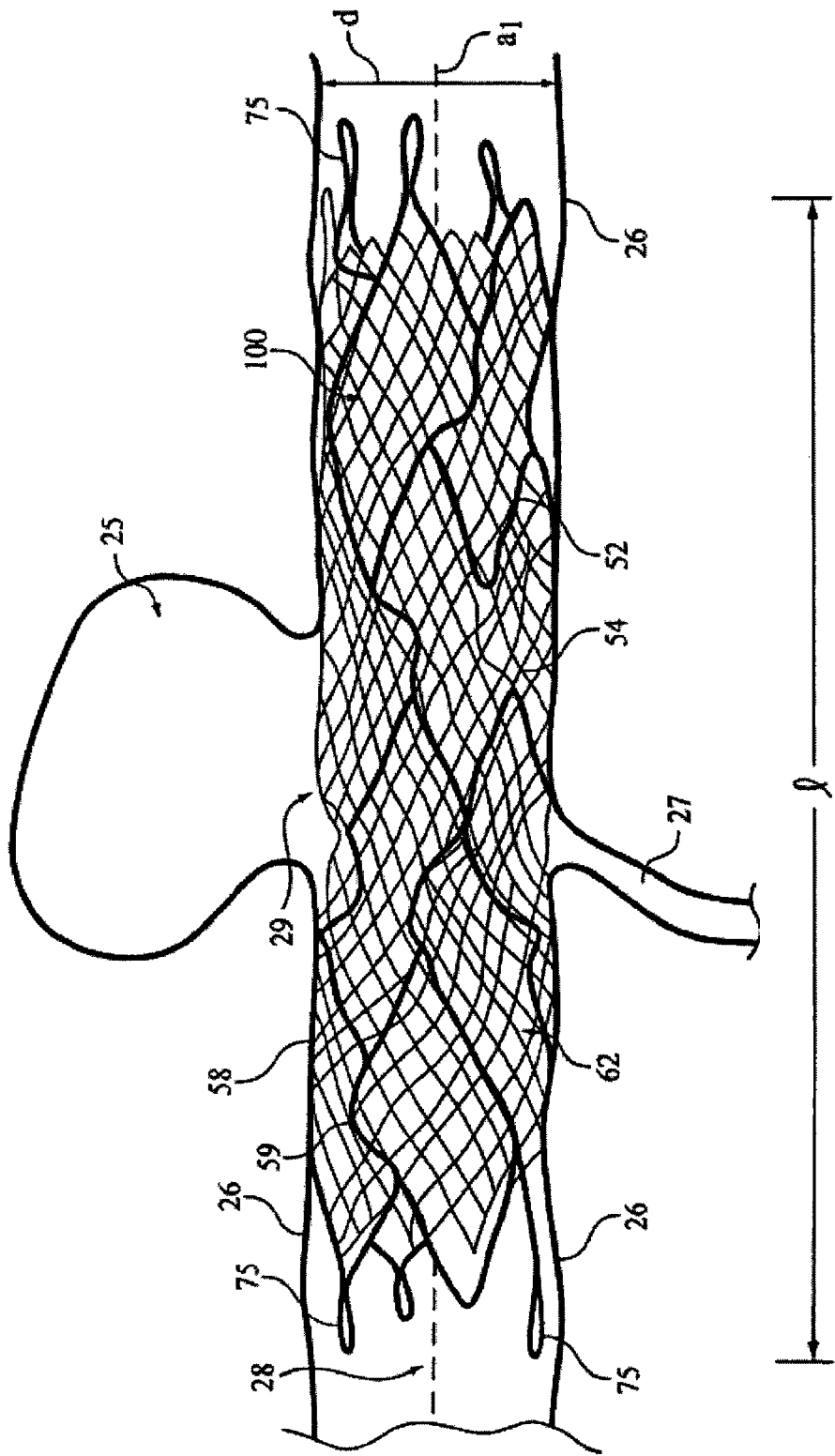
FIG. 1 is a side view of an endoprosthesis in a radially expanded state as deployed within a body passage adjacent an aneurysm.

Referring to FIG. 1, an endoprosthesis 100 is deployed within a body passage, e.g., within a vessel weakened by an aneurysm, e.g., an aneurysm 25 of a vessel 26 of a human brain. Endoprosthesis 100 includes a framework, e.g., a stent body 52, covered by a tubular member or cover 54. The stent body provides a relatively rigid framework that secures the endoprosthesis at the treatment site. The framework defines relatively large openings or fenestrations that contribute to the mechanical properties of the stent. The cover 54 is relatively thin and flexible and includes smaller fenestrations that contribute to the mechanical properties of the cover and occlude the fenestrations of the stent.

The endoprosthesis 100 modifies an amount or velocity of blood passing between vessel 26 and aneurysm 25. For example, prosthesis 100 can be deployed to reduce or block blood flow between vessel 26 and aneurysm 25. The endoprosthesis can also reduce blood flow from a feeder vessel 27. If so deployed, prosthesis 100 may sufficiently reduce blood flow to allow clotting or other healing processes to take place within aneurysm 25 and/or opening 29. Tubular member 54 can provide a greater attenuation of the blood flow into the aneurysm 25 than stent body 52 alone. Endoprosthesis 100, however, can allow some flow to pass between vessel 26 and aneurysm 25 even while providing some reduction in the rate and/or volume of flow. Prosthesis 100 can also (or alternatively) allow blood to pass between vessel 26 containing the prosthesis and adjacent vessels, e.g., feeder vessel 27, while still providing reduced flow with respect to the aneurysm.

Figure 2A:
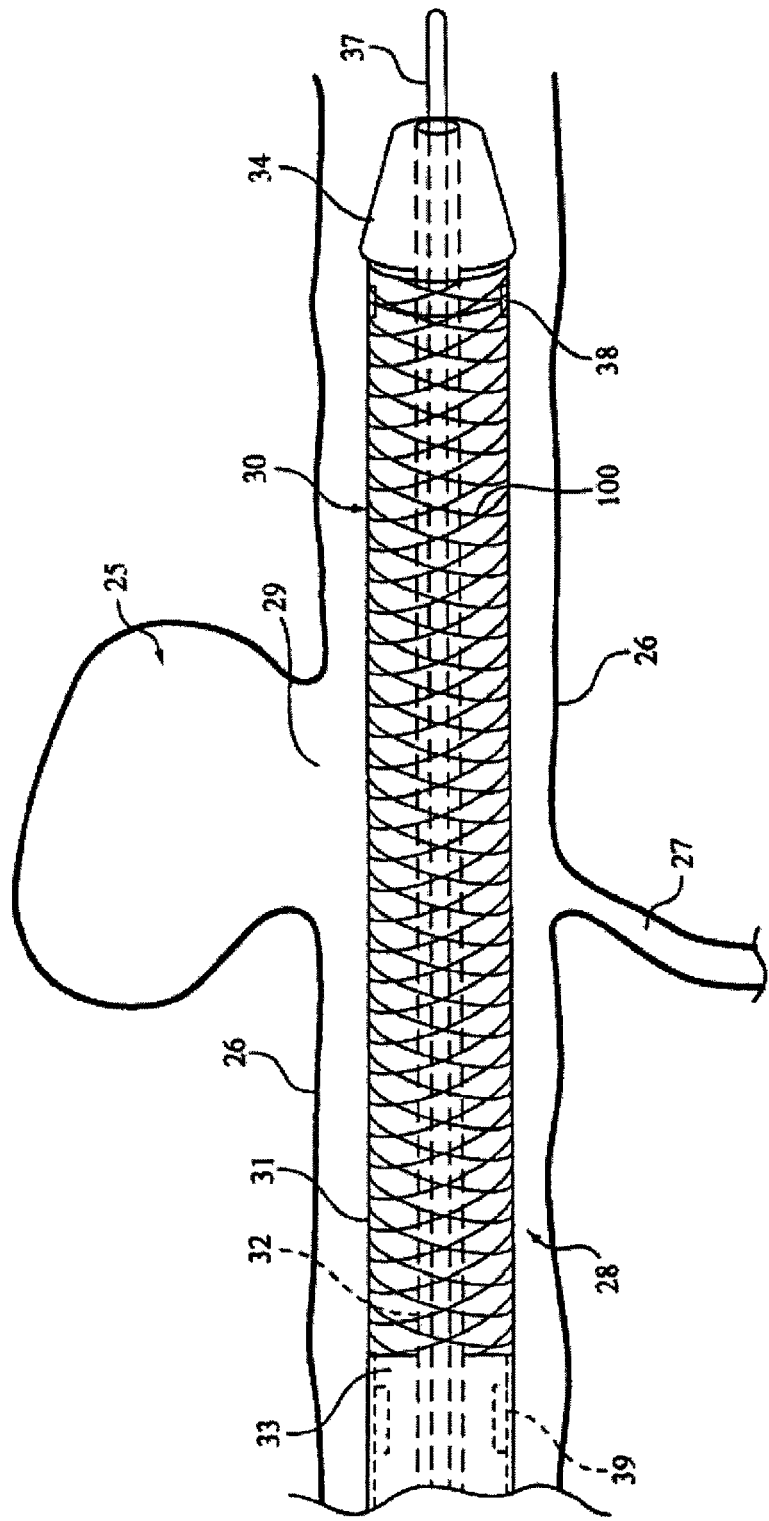
FIG. 2a is a side view of a distal portion of a deployment device prior to radial expansion of the endoprosthesis.
Figure 2B:
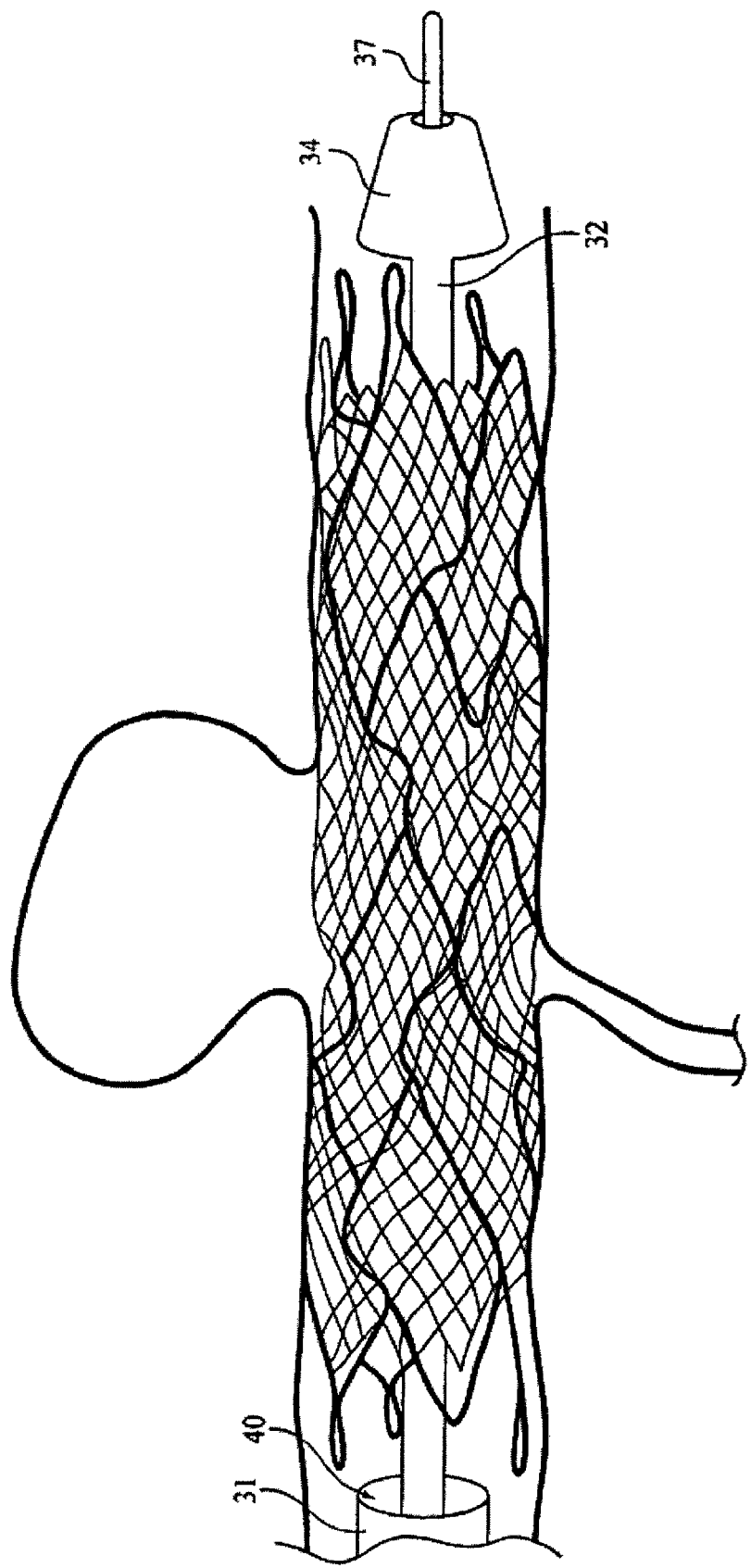
FIG. 2b is a side view of the distal portion of the deployment device subsequent to radial expansion of the endoprosthesis adjacent the aneurysm.

Referring to FIGS. 2a and 2b, endoprosthesis 100 is deployed to aneurysm 25 using a deployment device 30, such as a catheter that can be threaded through a tortuous pathway. The device 30 includes a retractable outer sheath 31 and an inner catheter 32. Device 30 is introduced over a guide wire 37 extending along the interior 28 of vessel 26. During introduction, the endoprosthesis 100 is radially compacted between outer sheath 31 and inner catheter 32 adjacent a distal opening 40 of the outer sheath.

Referring particularly to FIG. 2b, the outer sheath 31 is retracted upon reaching the desired deployment site, e.g., aneurysm 25. In some embodiments, endoprosthesis 100 self-expands by its own internal elastic restoring force when the radially restraining outer sheath is retracted. Alternatively, or in combination with self-expansion, deployment of prosthesis 100 may include use of a balloon or other device to radially expand prosthesis 100 within vessel 26. After deploying the endoprosthesis, the inner catheter 32 and guide wire 37 are withdrawn from vessel 26. Suitable delivery systems include the Neuroform, Neuroform2, and Wingspan Stent System available from Boston Scientific Target Therapeutics, Fremont, Calif. In embodiments, the outer sheath and/or inner catheter includes a reinforcing member to respectively resist elongation or compression as the outer sheath is withdrawn. Such reinforcing members include polymer shafts, braids, and coil structures.

Upon expansion, endoprosthesis 100 assumes a shape and radial extent generally coextensive with an inner surface of the vessel 26, e.g., a tubular shape centered about a longitudinal axis a1 of the prosthesis (FIG. 1). Depending upon the application, prosthesis 100 can have a diameter d of between, for example, 1 mm to 46 mm. In certain embodiments, a prosthesis for deployment within a vessel at an aneurysm can have an expanded diameter d of from about 2 mm to about 6 mm, e.g., about 2.5 mm to about 4.5 mm. Depending upon the application, prosthesis 100 can have a length along axis a1 of at least 5 mm, at least 10 mm, e.g., at least about 30 mm. An exemplary embodiment has an expanded diameter of about 3.5 mm and a length of about 15 mm. In embodiments, the stent body has a closed cell framework, an open cell framework, a helical framework, a braided framework, or combination thereof.

The cover can be fixed to the stent by, e.g. fasteners. Attachment techniques include brazing, welding or attachment with a filament, rivets or grommets, or crimping, or adhesive. In some embodiments, the tubular member differs from a fabric at least in that the tubular member lacks fibers that can be pushed apart to receive a filament as by sewing a fabric. Accordingly, the fenestrations can be formed prior to the process of passing the filament through the tubular member. Fenestrations that receive the filaments can be formed by, e.g., etching, laser cutting, or a photolithographic process. Attachment techniques are described in U.S. Ser. No. 11/025, 866, titled MEDICAL DEVICES INCLUDING METALLIC FILMS AND METHODS FOR MAKING SAME, filed contemporaneously herewith, which application is incorporated herein by reference.

The cover is formed of a thin film that exhibits advantageous properties such as strength, toughness, and flexibility by selection of the composition of the film, processing techniques, and mechanical configuration. For example, in particular embodiments, the film is a vapor-deposited material composed of a nickel-titanium alloy having a strength additive, e.g. chromium. The film has a thickness of about 50 μm or less, e.g. about 4-35 μm, and includes fine fenestrations, which facilitate collapsing the film to small diameter for delivery into the body and expansion at the treatment site, while impeding blood access to the aneurysm. In particular embodiments, the film is processed to modify dislocations, which contribute to strength and toughness of the thin film.

Deposited materials are formed by depositing film constituents from a suspended state, e.g. in a vapor or a vacuum onto a surface. In embodiments, the constituents are suspended, e.g. by bombarding, heating or sputtering a bulk target. The suspended constituents deposit on a substrate to form the film. Deposited films can exhibit highly uniform thickness and microstructure in very thin films, e.g. about 50 μm or less, e.g. 4-35 μm. Deposition techniques include sputter deposition, pulsed laser deposition, ion beam deposition and plasma deposition. Suitable deposition processes are described in Busch et al. U.S. Pat. No. 5,061,914, Bose et al. U.S. Pat. No. 6,605,111, Johnston U.S. Pat. No. 6,533,905, and Gupta et al. U.S. 2004/0014253, the entire contents of all of which are hereby incorporated by reference.

In particular embodiments, the deposited film is an alloy that includes nickel and titanium, and a strength additive or additives, which modify a mechanical property, e.g., a hardness or elasticity, of the film. In particular embodiments, the film is a tertiary alloy that has substantially no other components besides nickel, titanium, and additive present in an amount greater than 1%, 0.5% or 0.2% or less than 20%, 10%, or 5% by weight of the film. The film may consist essentially of nickel, titanium, and chromium. In embodiments, the deposited film includes between 54 and 57 weight percent nickel with the balance composed essentially of titanium and chromium. In some embodiments, a ratio of a weight of chromium of the film to a combined weight of nickel, titanium, and chromium of the film is at least 0.001, at least 0.002 e.g., at least 0.0025. The ratio of the weight of chromium of the film to the combined weight of chromium, nickel, and titanium of the film can be 0.02 or less, 0.01 or less, e.g., 0.0075 or less. The ratio of the weight of chromium to the combined weight of chromium, nickel, and titanium of the film can be about 0.0025. In embodiments, the alloy exhibits superelastic or pseudo-elastic properties. Superelastic or pseudo-elastic metal alloy, as described, for example, in Schetsky, L. McDonald, "Shape Memory Alloys," Encyclopedia of Chemical Technology (3rd ed.), John Wiley & Sons, 1982, vol. 20. pp. 726-736; and commonly assigned U.S. Ser. No. 10/346,487, filed Jan. 17, 2003.

A metallic film can be combined with one or more filaments in an endoprosthesis cover. Because the filaments and film may have very different mechanical properties, e.g., elongation before break and tensile strengths, the filaments and film cooperate to lend the cover desirable mechanical properties, e.g., toughness along the circumferential, radial, and/or longitudinal dimensions. In embodiments, a filament secures portions of a film relative to other portions of the film such as to maintain the three-dimensional shape of the cover and/or to secure the film with respect to a stent body.

Figure 3A:
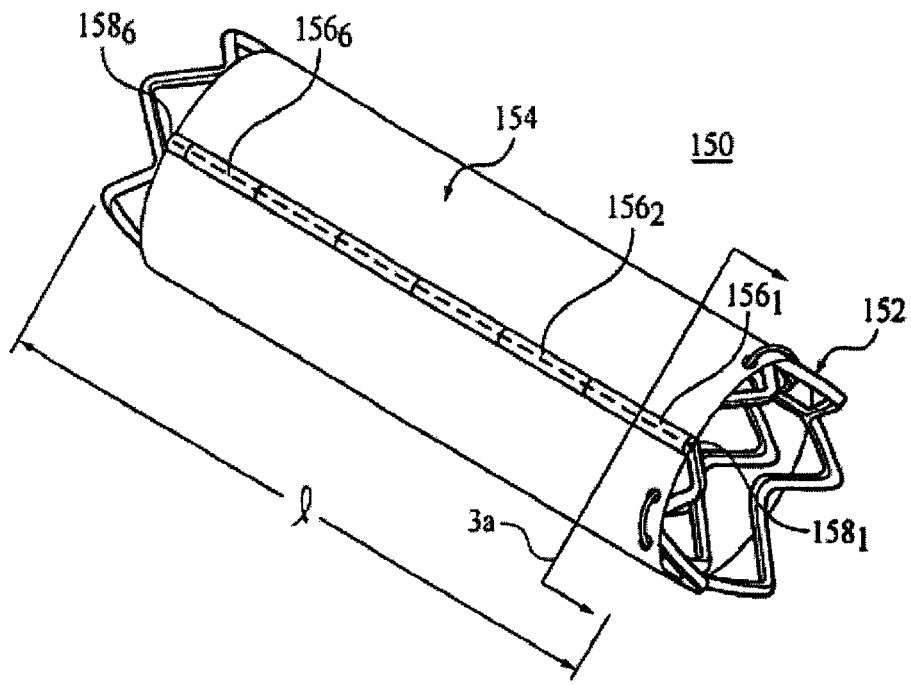
FIG. 3a is a perspective view of an endoprosthesis.
Figure 3B:
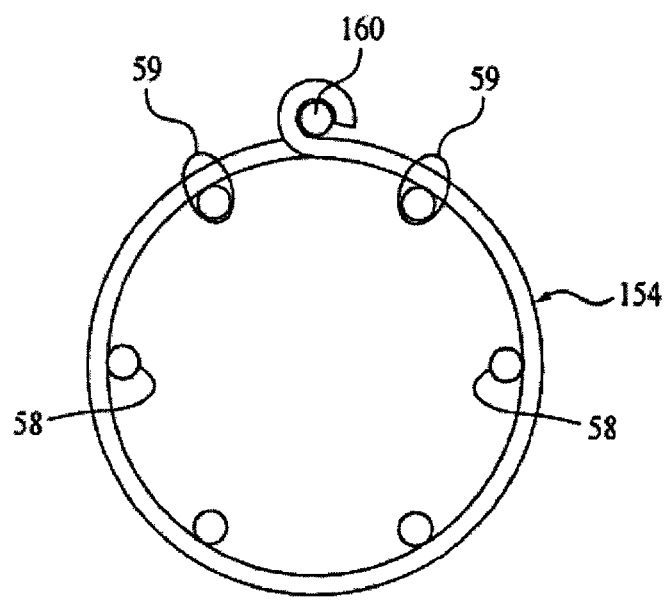
Figure 4:
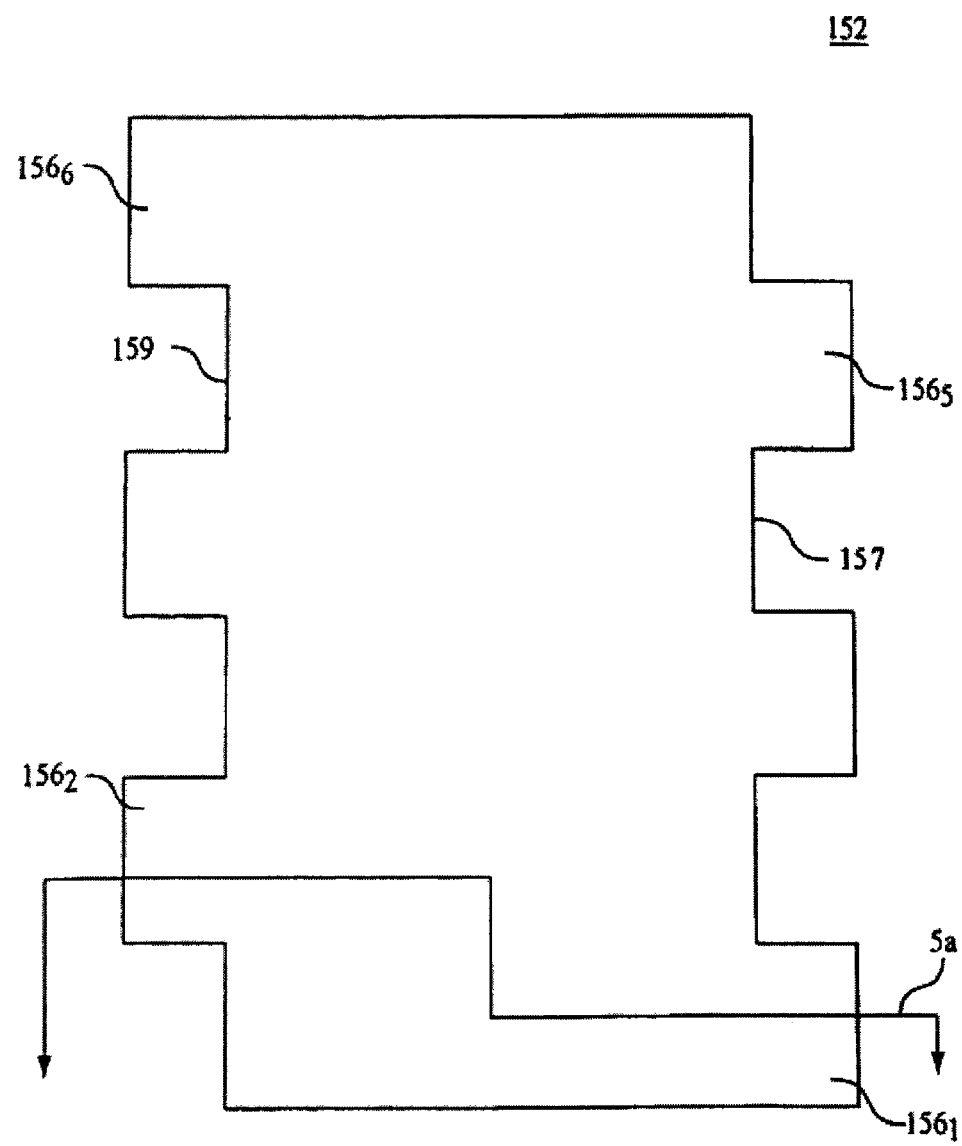
FIG. 4 is a top view of a cover of the endoprosthesis of FIG. 3a. The cover is shown in two-dimensions and separate from the endoprosthesis.

Referring to FIGS. 3a, 3b, and 4, an endoprosthesis 150 includes a cover 154 encircling a stent body 152. First and second edges 157 and 159 of cover 152 define a plurality of offset tabs 156i (FIG. 4). When formed as a cover, each tab defines a respective channel 158i (FIG. 3a). Different channels 158i are coaxial with one another parallel to a length 1 of cover 152. A filament 160 seen in FIG. 3b extends within the coaxial channels along the length 1 and prevents cover 154 from unrolling by securing offset tabs 156i relative to one another.

Filament 160 can include, e.g., a suture, a polymer, a textile, or a metal, e.g., a metal wire formed of gold, platinum, stainless steel, or a shape memory metal, e.g., nitinol. A filament can include a combination of such materials, e.g., a composite. The filament can be braided and need not have a circular configuration, e.g., the filament can be ribbon shaped. The filament typically has a thickness or radial dimension of less than a thickness of the film. In embodiments, the member is a metal wire having a diameter of about 10 μm or less, about 8μ, e.g., about 5 μm or less.

The filament 160 can have a higher tensile strength than the film of the cover 154. In embodiments, a ratio of the tensile strength of the filament 160 to the tensile strength of the film is at least about 1.5, e.g., at least about 2. The ratio may be about 4 or less, e.g., about 3 or less. The filament may be a nitinol wire having a tensile strength of at least 200 ksi, at least 250 ksi, e.g., at least 300 ksi. An exemplary metallic film has a tensile strength of 150 ksi.

In some embodiments, the filament 160 includes a wire of shape memory metal that is shape set differently from a shape set of the metallic film. In some embodiments, one of the member 160 and metallic film is shape set at a configuration corresponding to the radially compressed state within a delivery device while the other of the member and film is shape set at a configuration corresponding to the radially expanded state within a body passage. A primary difference in the shape set between the member 160 and the cover may be in the shape set length, with one of the member and cover having a longer shape set length than the other.

Figure 5A:
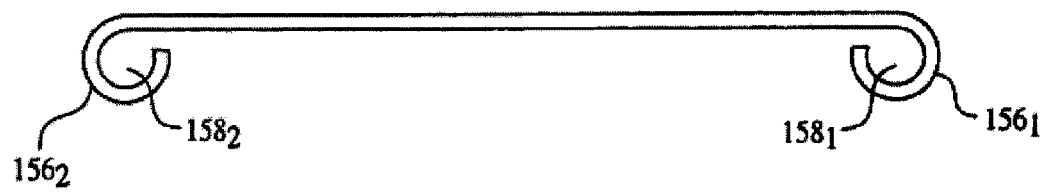
FIG. 5a is a cross-sectional end view of the cover of FIG. 4. Tabs of the cover have been formed into channels.
Figure 5B:
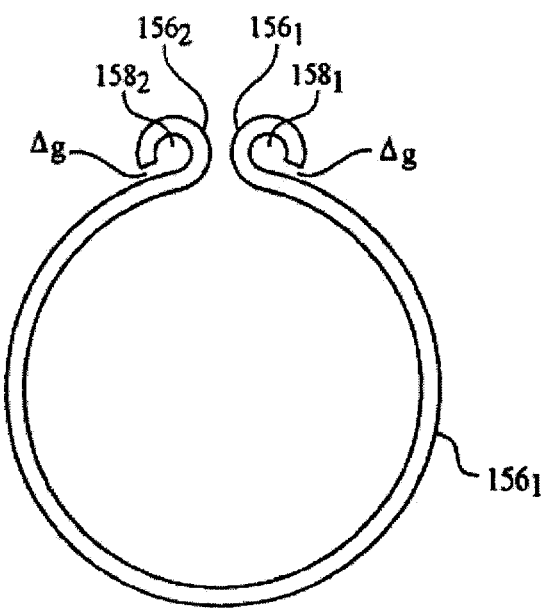
FIG. 5b is the cover of FIG. 5a. The cover has been formed into a generally tubular shape.

An exemplary method of manufacturing cover 154 includes depositing a metallic film on a substrate. The cover can be provided with fenestrations 62, which are not shown in FIG. 3a. Tabs 156i can be formed by photolithography or machined, e.g., by laser cutting, from a larger deposited film. Referring to FIG. 5a, each tab 156i is turned about itself to form a respective channel 158i. Referring to FIG. 5b, if not deposited on a three-dimensional substrate, the film can be rolled, e.g., about a mandrel, to provide a three-dimensional shape.

Adjacent tabs 156i are relatively secured by filament 160. The filament 160 can be inserted along the common axis of channels 158i or inserted laterally through a terminal gap Δg of each tab. If present, the terminal gap of each tab can be closed after introducing member 160. Either before or after positioning filament 160 with respect to tabs 156i, film 154 can be disposed with respect to a stent body, e.g., about the stent body (FIG. 3b). The cover and stent body can be relatively secured with, e.g., one or more filaments 59, which pass through fenestrations of the cover and engage framework members 58 of the stent body. In embodiments, some or all of the tabs engage a portion of the stent body, e.g., a framework member 58, to secure the cover and stent body.

In some embodiments, filament 160 and some or all of tabs 156i have little or no relative freedom of movement. For example, each tab 156i may mechanically engage filament 160 via a tight fit between respective channel 158i and the member 160. An adhesive or other polymer may also or alternatively be used to enhance the engagement between the filament and the channels of the tabs.

In embodiments, filament 160 and some or all of channels 158i allow some relative freedom of movement, e.g., longitudinal or circumferential freedom of movement. During radial compression and expansion of an endoprosthesis, the cover 154 and filament 160 move relatively to accommodate different length changes without deforming the cover or endoprosthesis. Longitudinal freedom of movement may be provided by a filament not tightly engaged by the channels, e.g., by a filament having a diameter smaller than an inner diameter of the channels. Circumferential freedom of movement can be provided by circumferentially elongating the channels so that the cover edges 157,159 can move circumferentially relative to one another, e.g., toward and away from one another. Adjacent tabs 156i and 156i±1 may define gaps (not shown) to allow the cover edges some relative longitudinal freedom of movement. An elastic polymer may fill the channels to help retain the filament yet allow some relative movement.

Channels 158i are shown as extending coaxially the entire length of the cover. In some embodiments, channels 158i extend along only a portion of the cover length, e.g., ½ the length or less, ⅓ the length or less, or ¼ the length or less. The resulting "shorter" channel may be located anywhere along the length of the endoprosthesis, e.g., centrally or distally or proximally relative to an implanted prosthesis.

Channels 158i are shown as generally parallel with a longitudinal axis of the endoprosthesis 150. In embodiments, the channels 158i and filaments can have other configurations, e.g., circumferential, curved, or helical about the endoprosthesis.

Figure 6:
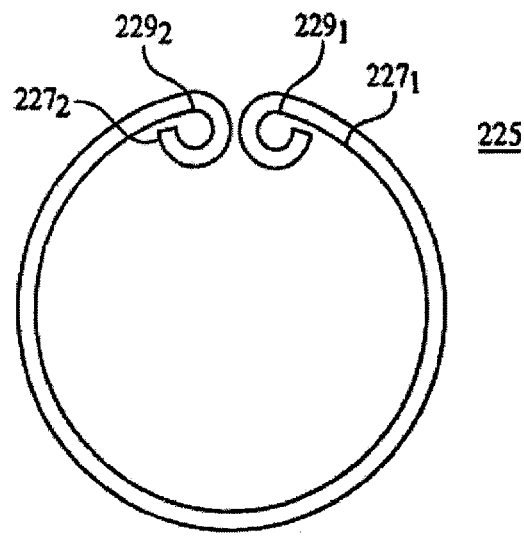
FIG. 6 is a cover suitable for an endoprosthesis. The cover includes tabs forming channels, which are located within a circumference of the cover.

Referring to FIG. 6, a cover 225 includes tabs 227i and channels 229i located within an external circumference of the cover. Accordingly, when relatively secured and placed concentrically with respect to a stent body, the cover forms a relatively smooth outer surface with little or no ridge-like protrusion resulting from the tabs 227i. Channels 229i may also be used to engage a framework member 58 of a stent body, which engagement can secure the cover and stent body.

Figure 7:
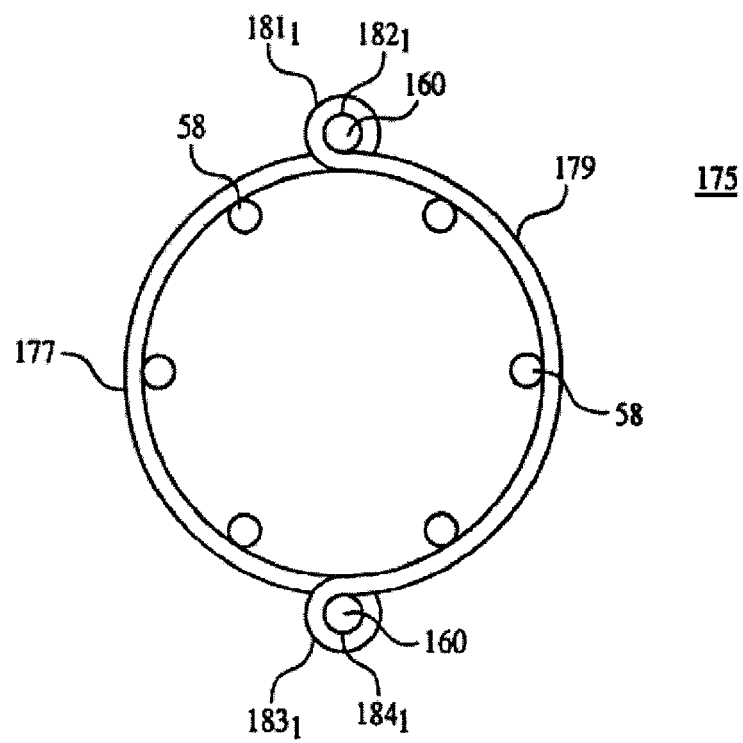
FIG. 7 is an endoprosthesis having a cover formed of two cover portions.

Referring to FIG. 7, a cover 175 having first and second cover portions 177,179 encircles a stent body having framework members 58. Each cover portion defines first and second edges. First edges and second edges of cover portions 177, 179 are secured to one another by first and second sets of offset tabs 181i,183i, which form respective channels 182i, 184i. The channels of different tabs are coaxial aligned and extend along at least a portion of the length of the endoprosthesis. A filament 160 extends along the coaxial channels. Although only two cover portions are shown, an endoprosthesis can have even more cover portions, e.g., 3 or more, 4 or more, or 5 or more, which combine to form a generally tubular cover.

Cover portions 177,179 may have some freedom of movement relative to one another. For example, by allowing longitudinal or circumferential freedom of movement between different cover portions, an endoprosthesis can accommodate delivery or deployment within a tortuous body passage having small radius curves. Freedom of movement between the cover portions can be provided using, e.g., the techniques described for providing relative freedom of movement between a filament and cover.

Figure 8:
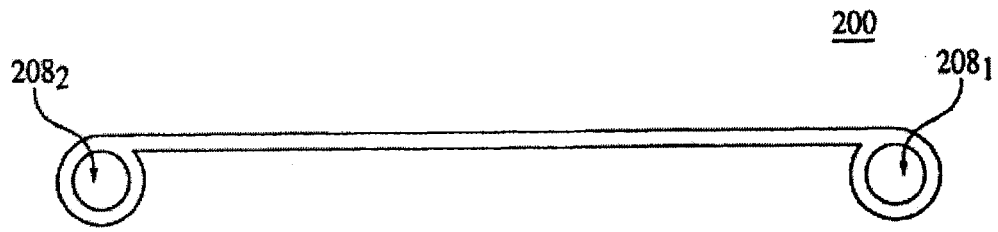
FIG. 8 is a cover having channels formed via metallic film deposition.
Figure 9:
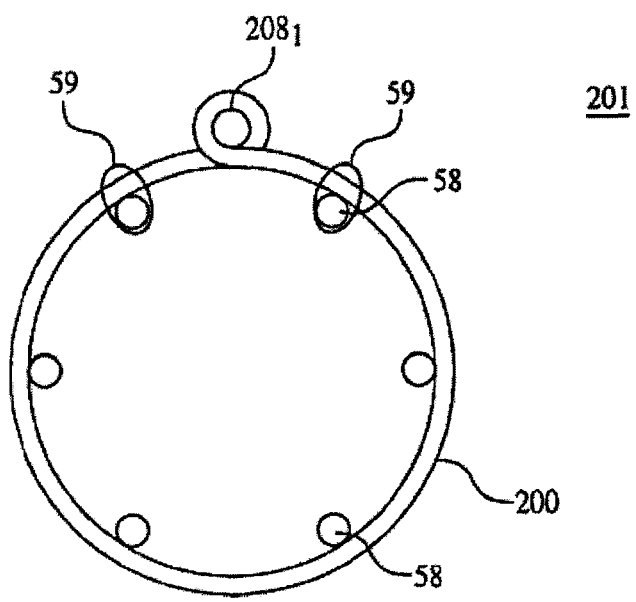
FIG. 9 is a cross-sectional view of an endoprosthesis including the cover of FIG. 8.

Referring to FIGS. 8 and 9, an endoprosthesis cover 200 includes tabs having integral channels 208i formed by, e.g., three-dimensional deposition over a sacrificial medium. Each integral channel defines a complete circumference without a seam resulting from mechanical channel formation. An endoprosthesis 201 is formed by positioning the cover 200 about a stent body having framework members 58 and securing the tabs with a filament 160 (FIG. 9).

An exemplary method of manufacturing cover 200 includes depositing a first layer of metallic film on a substrate, whether two- or three-dimensional. A sacrificial medium, e.g., chromium, is photolithographically deposited over portions of the previously deposited film.

The sacrificial medium is formed of a material, e.g., chromium, that can be removed, e.g., by etching, from the metallic film without damage thereto. Additional material of the metallic film is deposited over the sacrificial medium to complete the film. Subsequently, the sacrificial medium is removed from the remaining film leaving behind the integral channels.

Figure 10A:
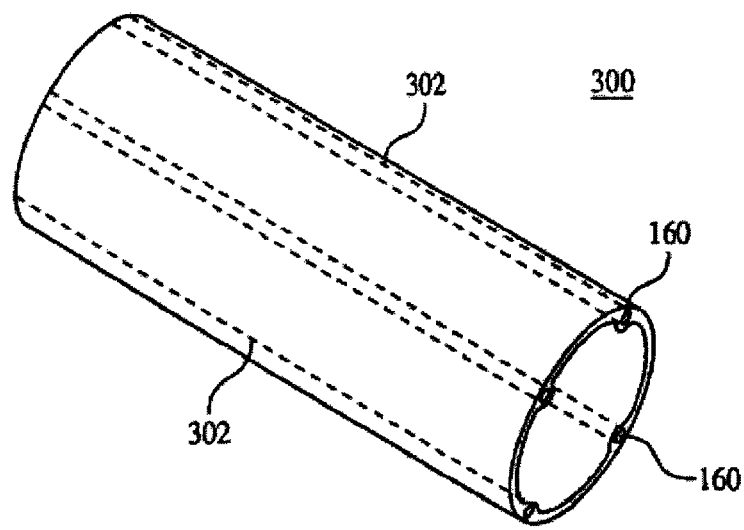
FIG. 10a shows an endoprosthesis having a plurality of integral, longitudinally extending filaments.
Figure 10B:
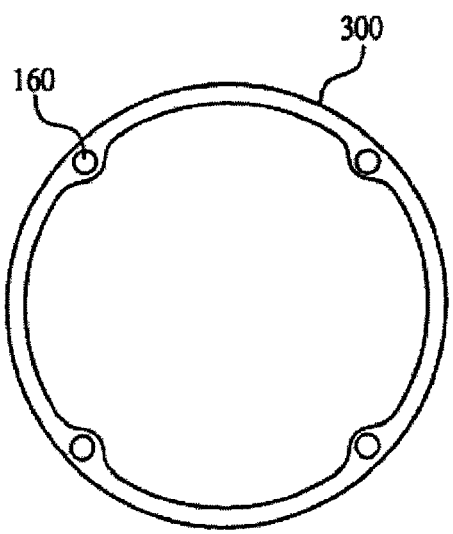

Referring to FIGS. 10a and 10b, a cover 300 (shown without a stent body) includes longitudinal channels 302 each formed by depositing metal about a filament 160. In this embodiment, the filament is typically a metal ribbon or wire, e.g., a metal wire of shape memory alloy. Depositing the metallic film about the wire secures the two together and ensures that the mechanical properties of each are communicated to the other without losses resulting from slippage. Although filaments 160 are shown as extending linearly along the longitudinal axis of the endoprosthesis, one or more of the filaments can have other longitudinally extending configurations, e.g., circumferential, curved, or helical. Filaments may intersect or cross one another. In other embodiments, some or all the wires do not intersect or cross another wire.

An exemplary method for forming cover 300 includes depositing a first layer of metallic film. Wires 160 are positioned adjacent the deposited film. Additional metal is deposited over the wires to integrate the wires and film. In an alternative method, wires 160 are positioned over a substrate. A first amount of metallic film is deposited over the wires and substrate. Subsequently, the first amount of film and substrate are separated and additional metal film is deposited to integrate the wires and film.

Figure 11:
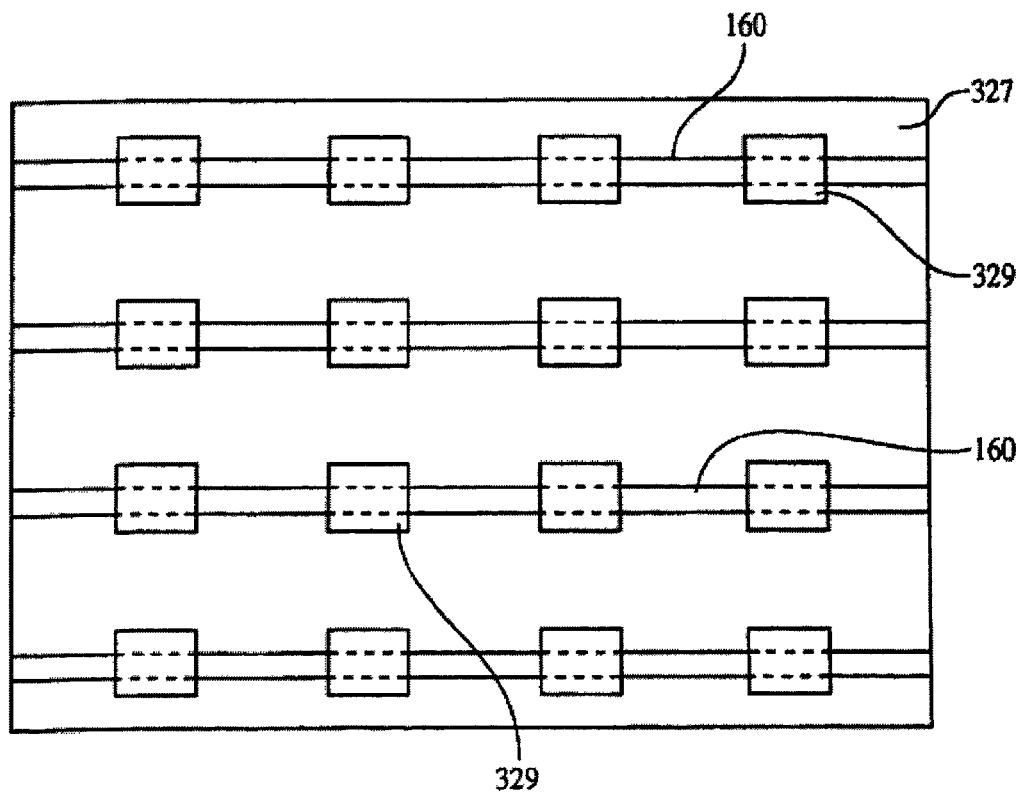
FIG. 11 is a cover suitable for an endoprosthesis. The cover has a plurality of longitudinally extending filaments each having a plurality of embedded integral portions and a plurality of exposed portions.

Referring to FIG. 11, a cover 325 includes a plurality of partially exposed filaments 160. Portions of the filaments 160 are embedded within a deposited metallic film of the cover and other portions of the filaments are left exposed. When formed about a stent body, the exposed portions of wire 160 can engage framework members of the stent body to secure the cover and stent body together. Another filament, e.g., a suture or wire, can be threaded through exposed portions of filaments 160 to secure the cover to a stent body or to retain the cover in a three-dimensional shape.

In some embodiments, a deposited thin film and including one or more filaments is useable as an endoprosthesis without a supporting stent. For example, an endoprosthesis without a supporting stent can include a deposited thin film including one or more at least partially embedded wires contributing to radial and/or longitudinal strength of the film.

In some embodiments, the filaments, whether embedded or not, extend beyond an end of the endoprosthesis. The extending filaments can be used to, e.g., re-sheath the endoprosthesis in order to change its position or withdraw it from a lumen, or to pull the endoprosthesis along a body lumen.

In the embodiment shown, an endoprosthesis has a generally tubular shape. In some embodiments, however, the endoprosthesis (or stent body 52 or tubular member 54 individually) has or includes other shapes such as conical, oblate, and branched. The endoprosthesis may have a closed end to form, e.g., a basket shape. Thin films, discussed above, composed of Ni—Ti-strength additive alloys and/or with modified microstructures, can be used in other applications. Examples include baskets, filters, catheters, guidewires, and medical balloons, such as an angioplasty balloon. Filaments of such endoprostheses may intersect or be woven to define a shape of the endoprosthesis.

Other examples of endoprostheses including a thin film as well as related systems and methods are described in U.S. provisional patent application No. 60/549,287, filed Mar. 2, 2004, which application is incorporated herein by reference.

An endoprosthesis may include a cover disposed externally to a framework as shown and/or internally of a framework. Endoprostheses having a cover including, e.g., a deposited thin film, disposed internally of a framework are described in U.S. patent application Ser. No. 11/025,464, titled MEDICAL DEVICES INCLUDING METALLIC FILMS AND METHODS FOR MAKING SAME, and filed concurrently herewith, which application is incorporated herein by reference.

An endoprosthesis may include features to enhance a flexibility of the endoprosthesis as described in U.S. patent application Ser. No. 11/025,158, titled MEDICAL DEVICES INCLUDING METALLIC FILMS AND METHODS FOR MAKING SAME, and filed concurrently herewith, which application is incorporated herein by reference.

The composition and/or fabrication method of a deposited thin film of an endoprosthesis may include features that enhance a strength or toughness of the film as described in U.S. patent application Ser. No. 11/025,860, titled MEDICAL DEVICES INCLUDING METALLIC FILMS AND METHODS FOR MAKING SAME, and filed concurrently herewith, which application is incorporated herein by reference.

An endoprosthesis may include a deposited thin film and a polymer as described in U.S. patent application Ser. No. 11/025,867, titled MEDICAL DEVICES INCLUDING METALLIC FILMS AND METHODS FOR MAKING SAME, and filed concurrently herewith, which application is incorporated herein by reference.

Methods for loading an endoprosthesis into a delivery device and systems for delivering an endoprosthesis to a treatment site are described in U.S. patent application Ser. No. 11/025,660, titled MEDICAL DEVICES INCLUDING METALLIC FILMS AND METHODS FOR LOADING AND DEPLOYING SAME, which application is incorporated herein by reference.

All publications, references, applications, and patents referred to herein are incorporated by reference in their entirety.

Other embodiments are within the claims.

What is claimed is:

1. An endoprosthesis, comprising:
   a metallic film defining first and second opposed surfaces and a thickness of less than about 50 μm therebetween; and at least one filament, the at least one filament defining a length, at least two portions of the filament along its length being embedded within the metallic film between the first and second surfaces, the two portions being separated by a non-embedded portion of the filament.

2. The endoprosthesis of claim 1, wherein the metallic film comprises titanium and nickel.

3. The endoprosthesis of claim 1, wherein the metallic film has a substantially tubular shape defining a longitudinal axis and the at least one filament extends generally along the longitudinal axis.

4. The endoprosthesis of claim 3, wherein the tubular shape of the metallic film defines a length along the longitudinal axis and the length of the at least one filament is at least about 30% of the length of the tubular shape of the metallic film.

5. The endoprosthesis of claim 4, comprising a plurality of filaments each defining a length, at least a portion of each filament along its length being embedded within a metal alloy between the first and second surfaces of the metallic film, each filament extending generally along the longitudinal axis of the metallic film, the length of each filament being at least 30% of the length of the tubular shape of the metallic film.

6. The endoprosthesis of claim 4, wherein at least 75% of the filament along its length is embedded within a metal alloy between the first and second surfaces of the metallic film.

7. The endoprosthesis of claim 4, wherein the at least one filament comprises an alloy comprising nickel and titanium.

8. The endoprosthesis of claim 7, wherein the metallic film and the at least one filament each have a respective tensile strength, the tensile strength of the at least one filament being greater than the tensile strength of the metallic film.

9. An endoprosthesis, comprising:
   a metallic film defining first and second opposed metallic film edges, the first and second opposed metallic film edges each defining a channel; and
   at least one filament, the at least one filament extending through the channel of each opposed metallic film edge.

10. The endoprosthesis of claim 9, wherein the metallic film comprises nickel and titanium.

11. The endoprosthesis of claim 9, wherein the metallic film has a substantially tubular shape defining a longitudinal axis and the at least one filament extends generally parallel to the longitudinal axis.

12. The endoprosthesis of claim 11, wherein the tubular shape defines a length along the longitudinal axis and the length of the at least one filament is at least about 30% of the length of the tubular shape.

13. The endoprosthesis of claim 11, wherein the first and second opposed edges each define at least one offset tab, the channel of each opposed edge being formed by the offset tab.

14. The endoprosthesis of claim 13, wherein the first and second opposed edges each define a plurality of channels, each channel being formed by a respective offset tab, the at least one filament extending through at least some of the channels of each opposed edge.

15. The endoprosthesis of claim 11, wherein the endoprosthesis comprises a stent body, at least a portion of the at least one filament and at least a portion of the stent body being secured together.

16. The endoprosthesis of claim 11, wherein the at least one filament defines a longitudinal axis, an engagement between at least one of the channels and the at least one filament restricting movement of the at least one filament along its longitudinal axis with respect to the at least one of the channels.

17. The endoprosthesis of claim 11, wherein the first and second opposed edges are a first pair of opposed edges and the metallic film defines a plurality of pairs of first and second opposed edges, each edge of each pair defining at least one channel, a respective filament extending through the channel of each opposed edge of each pair.

18. The endoprosthesis of claim 17, wherein each pair of opposed edges extends generally along the longitudinal axis of the metallic film and the at least one filament has a length at least about 30% of the length of the tubular shape.

19. The endoprosthesis of claim 18, wherein the first and second edges of each pair of opposed edges have at least some relative freedom of movement with respect to a circumference of the metallic film.

20. A method of manufacturing an endoprosthesis, comprising:
   embedding at least two portions of a filament along a length of the filament within a metallic film, the two portions being separated by a non-embedded portion of the filament,
   wherein the metallic film defines first and second opposed surfaces and a thickness of less than about 50 μm there between, and the at least a portion of the filament is embedded within the metallic film between the first and second surfaces.

21. A method of manufacturing an endoprosthesis, comprising:
   forming a metallic film defining first and second opposed metallic film edges, the first and second opposed metallic film edges each defining a channel; and
   extending a filament through the channel of each opposed metallic film edge.

* * * * *